United States Patent
Foser

[11] Patent Number: 6,039,566
[45] Date of Patent: Mar. 21, 2000

[54] METHOD OF PRODUCING DENTURES AND ARTICULATOR FOR USE THEREWITH

[75] Inventor: Hanspeter Foser, Balzers, Liechtenstein

[73] Assignee: Ivoclar AG, Schaan, Liechtenstein

[21] Appl. No.: 09/145,070

[22] Filed: Sep. 1, 1998

[30] Foreign Application Priority Data

Sep. 8, 1997 [DE] Germany .......................... 197 39 220

[51] Int. Cl.⁷ ................................................. A61C 11/00
[52] U.S. Cl. ............................ 433/60; 433/215; 433/167
[58] Field of Search .............................. 433/34, 37, 213, 433/214, 60, 47, 167, 215

[56] References Cited

U.S. PATENT DOCUMENTS

| | | | |
|---|---|---|---|
| 2,358,730 | 9/1944 | Nelson et al. | 433/34 |
| 2,629,929 | 3/1953 | Lavine et al. | 433/60 |
| 3,251,909 | 5/1966 | Pickands et al. | 433/34 |
| 4,252,523 | 2/1981 | Gatso | 433/60 |
| 4,681,543 | 7/1987 | Monroy | 433/167 |
| 4,932,869 | 6/1990 | Bergeron | 433/167 |
| 5,403,186 | 4/1995 | Ginsburg | 433/167 |

FOREIGN PATENT DOCUMENTS

| | | |
|---|---|---|
| 40 28 728 | 3/1992 | Germany . |
| 195 10 550 | 10/1995 | Germany . |

OTHER PUBLICATIONS

Max Bosshart, Das Einbetten und das Stopfen, Dental–Labor, Dec. 1995 vol. XLIII, pp. 2004–2008, 2011–2014.

*Primary Examiner*—Todd E. Manahan
*Attorney, Agent, or Firm*—Alan S. Korman; John C. Thompson

[57] ABSTRACT

A method of producing dentures is provided. A moldable denture plate is introduced into the mouth of a patient. Deformation of the denture plate is carried out in a patient-specific manner. While the denture plate is still in the patient's mouth, it is subjected to at least a preliminary hardening. After being removed from the patient's mouth, the denture plate is provided with prefabricated teeth.

15 Claims, 1 Drawing Sheet

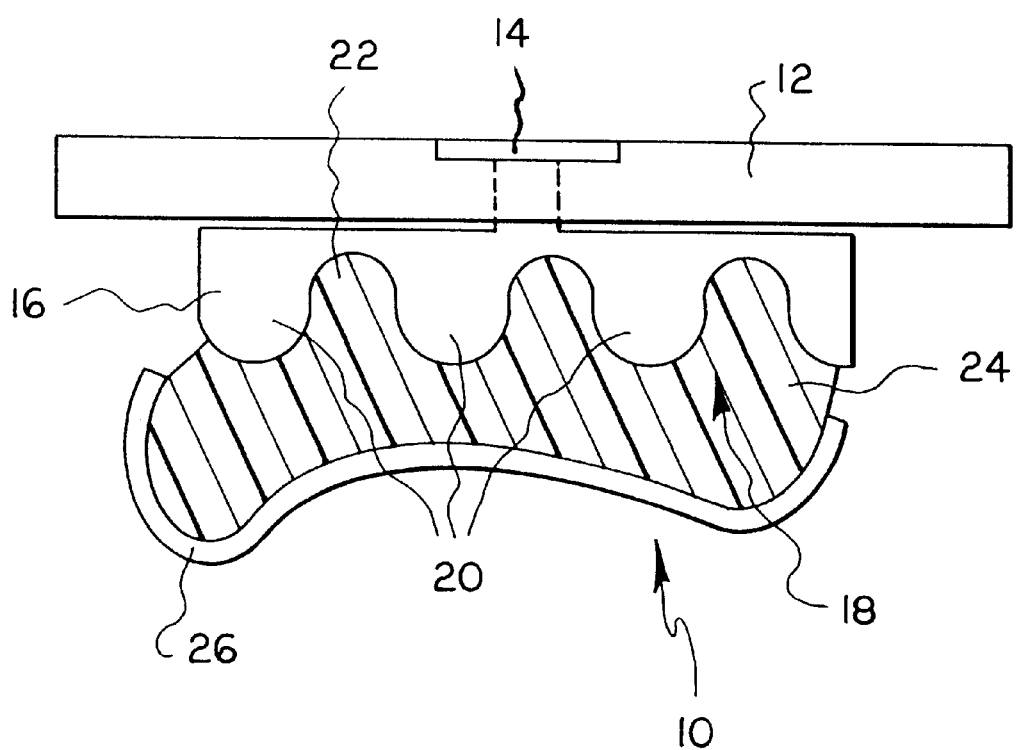

METHOD OF PRODUCING DENTURES AND ARTICULATOR FOR USE THEREWITH

BACKGROUND OF THE INVENTION

The present Invention relates to a method of producing a tooth prothesis or denture, where a moldable or deformable denture plate is introduced into the mouth of a patient and is subjected to hardening. The present invention also relates to an articulator having an in particular retention member.

The conventional production of total dentures, which can be removed from the mouth of a patient, requires a number of complicated measures in order to ensure a precise fit of the denture. For example, it is necessary to mold the mouth situation and to produce a model, and based upon this situation to produce a positive mold, for example in plaster of Paris, that is utilized for producing the denture. In this connection, a number of special steps are necessary. For example, it is necessary to seal the plaster of Paris and teeth in order to remove the polymerized synthetic material and the teeth, which are made of ceramic material or also of synthetic material, from the plaster of Paris.

A vessel is utilized for the production of the denture, whereby pressures of up to 3 tons are required. Despite the up to now undertaken expense, frequently so-called bite elevations occur; in other words, an elevation of the position of the teeth in the submillimeter range, whereby it is known, for example, from "Dental-Labor" volume 12/95, page 2003 et seq, to use an annular channel in order to reduce the bite elevation to a tolerable level.

Such methods are regularly used at the present time for the basic provision of a total denture. A further known method, the injection method, does not bring about a bite elevation; however it is technically far more complicated and requires a very exact handling by the dental technician, already for the reason of avoiding the formation of bubbles. Due to the expense, this method has found only limited use. Various other methods have been proposed in order to improve the casting and injection methods. For example, it Is know from DE-OS 40 28 728 to use a gel or silicone in order to enable a direct light polymerization of the denture in the casting mold. However, this method results in unsatisfactory dentures, because the gel or silicone is too soft so that deformations easily occur.

A fabricated denture has also been proposed in DE 195 105 50 A1 that is to be lined in a patient-specific manner. However, maintaining prefabricated dentures requires a lot of storage space if a somewhat satisfactory adaptation to specific patient requirements is to be undertaken. If merely a few models are to be prefabricated, correspondingly thick linings or underlays must be provided, which significantly increases the thickness of the denture and is hence unsatisfactory for the wearing comfort of the denture.

It has furthermore also been proposed to use a prefabricated denture base that is introduced in a deformable state into the mouth of the patient where it should be adjusted. For this purpose, a mixture is compacted under high pressure and a temperature of about 150° C. and is then heated to about 60° C. and introduced into the mouth of the patient. There is then effected a preliminary adjustment, and in addition a lining material is applied and a denture plate is again introduced into the patient's mouth. The denture plate is then removed, partially hardened, reintroduced into the mouth of the patient, and finally again removed and finish hardened. Teeth can be mounted either before or after the start or end of the introduction of the denture into the patient's mouth.

With this known method it is therefore necessary to introduce the denture plate at least three times into the patient's mouth, whereby the patient is additionally confronted with various materials. The patient therefore tends to get the impression that touch-ups are necessary, so that the patient acceptance and hence also the acceptance of the treating dentist are unsatisfactory. Despite this complicated procedure, imprecision easily results, whereby in addition the introduction of hot synthetic or polymeric material at nearly 60° C. into the oral cavity is unpleasant.

It is therefore an object of the present invention to provide a method and articulator of the aforementioned general types where on the one hand a bite elevation is reliably avoided, and on the other hand there is ensured that the patient acceptance is improved, whereby nonetheless the expense relative to conventional manufacturing processes of dentures should be reduced so that the denture can be manufactured in a considerably easier manner.

SUMMARY OF THE INVENTION

The method of the present invention is characterized primarily by introducing a moldable denture plate into the mouth of a patient, carrying out a deformation of the denture plate in a patient-specific manner, then while still in the mouth of the patient subjecting the denture plate to at least a preliminary hardening, and after removing the denture plate from the patient's mouth providing the denture plate with prefabricated teeth.

In contrast to heretofore known methods, the inventive method offers the enormous advantage that a total denture, or if necessary also a partial denture, can be produced with high precision and yet at reduced cost relative to the conventional technology. For this purpose, pursuant to the present invention the denture plate is made of deformable polymeric material, is introduced into the mouth of the patient and is then adapted to the jaw. The light hardening synthetic or polymeric material is prehardened and then removed, so that the precise shape of the basal surface of the denture is already fixed in the mouth of the patient and it is therefore not necessary to introduce the denture plate into the patient's mouth, thus eliminating having to "touch up" the shape. The denture plate is then preferably still post hardened, whereby it is to be understood that alternatively it would be possible to undertake complete hardening of the denture plate in the patient's mouth.

A denture plate is preferably delivered between two light proof thin sheets or foils in the maximum size required in the practice whereby prior to introduction into a patient's mouth the denture plate is either selected in a patient-specific manner, or is brought to the desired size by removing the edges. If necessary, anything projecting from the side can later be readily removed.

The inventive approach surprisingly results in an improved precision relative to the conventional state of the art, whereby for the latter this is also due to the imprecision that results from the taking of impressions and from the production of models, and the subsequent production of the denture by an injection process or a casting process with a vessel, and which can be avoided with the present invention.

The inventive process enables the use of conventional articulators or, if necessary, bite position holders as well as the conventional bite position determination. Pursuant to a particularly advantageous feature of the present invention, the denture plate or denture base can be introduced by means of a special base that is easy to remove yet is precisely held, whereby the basal surface is preferably filled with silicone or some other elastic material, and this material positively engages In a corresponding base of an articulator. The silicone material can later be readily removed, yet enables the precision required during alignment in the articulator.

Pursuant to a particularly advantageous embodiment of the present invention, the teeth are positioned in wax-like synthetic material. The tooth positioning, and if necessary a correction, are then checked, whereby pursuant to the present invention it is particularly expedient that the synthetic or polymeric material hardens together with the final polymerization by light hardening. It is to be understood that in place thereof, a conventional placement in the Vorwall technique with the aid of wax is also possible, with this wax then later being boiled out and being replaced by polymeric material. The polymeric material required for this can preferably be kept readily available in an easy to handle manner in a tube in paste form.

Further specific features of the present invention will be described in detail subsequently.

BRIEF DESCRIPTION OF THE DRAWING

The objects and the advantages of the present invention will appear more clearly from the following description of one exemplary embodiment in conjunction with the accompanying schematic drawing, which is a partially illustrated articulator for carrying out one step of the inventive process.

DESCRIPTION OF PREFERRED EMBODIMENTS

With the inventive method, a prefabricated dental plate or base, which is intended for the toothless upper or lower jaw, is first selected in a patient-specific manner; the prefabricated, semicircular or U-shaped plate can be about 1.5–3 mm thick. The denture plate comprises a polymethylmethacrylatelmethyl-methacrylate that is moldable and light hardening more specifically a mixture from polymethylmethacrylate powder and methylmethacrylate liquid, the viscosity depending upon the mixture ratio of the elements.

The material is selected in such a way that the requirements with respect to ease of moldability, precise reproduction of detail, and long shelf life are fulfilled, whereby in addition the material should be tasteless and should not irritate tissue. The denture base is introduced into and pressed against the mouth of the patient, approximately at body or room temperature, so that the basal surface forms exactly to the roof of the mouth or the lower jaw of the patient.

Pursuant to a modified specific embodiment of the inventive method, after this initial adaptation a pasty synthetic material is partially applied that serves as the lining or underlay, as a result of which a fine adaptation is effected.

While still in the mouth of the patient, the denture plate is then hardened with a light hardening apparatus, for example the "Vivalux" apparatus of the company Ivoclar AG, Liechtenstein, at least to such an extent that when the denture is handled and removed from the mouth, it can no longer deform. The inventive method provides the particular advantage that already in the mouth the exact shape fundamentally exists, so that the errors that result with known methods during removal from the mouth, and also the errors that result during model casting, are reliably avoided.

After the denture plate is removed from the pattent's mouth, it is placed in a specially adapted articulator, for example, the STRATUS 200 of the company Ivoclar AG, Liechtenstein.

Referring now in particular to the drawing, the upper portion of the articulator 10 has a support plate 12 that is provided with a central fastening means 14, The support plate 12 can also be adjustable, so that it can be more easily fitted to variously sized denture plates.

The central fastening means 14 enables a reliable mounting of a special inventive base 16. The underside of the base 16 has a profiled surface 18 with projections or raised portions 20 and recesses 22 that alternate with one another. The surface 18 has no undercuts and is hence also very favorable to produce. The surface 18 serves for holding a material 24 in a laterally interlocking and vertically frictionally engaging manner; the material 24 is preferably elastic and is in particular formed of silicone.

The material 24 is furthermore received in the formed denture plate 26, with the application being effected in such a way that the approximately shell-shaped denture plate 26 is satisfactorily filled with the material 24, whereupon it can be pressed against the base 16. The material 24 then penetrates into the recesses 22 where it adheres as long as desired, although it can again be easily removed by tipping it toward the side. In the same way, the material 24 can be removed from the denture plate without leaving any residue.

This way of mounting the denture plate 26 permits a reliable securement to the articulator, so that the positioning of the teeth, and the further steps can be effected in a known and reliable manner.

The teeth can be delivered either as a block of teeth that are prefabricated and flexibly interconnected, or as individual teeth whereby it is also possible to undertake a test in the mouth after the teeth have been positioned.

Positioning of the teeth can be effected either with wax or paraffin, that must later be boiled, out and is replaced by polymeric material in the knownVorwall technique, or is effected right away in pasty, wax-like polymeric material that can be hardened by light; if necessary the positioning can be corrected.

After the final positioning, the teeth are keyed with silicone or some other material, such as plaster of Paris; in other words they are fixed in position relative to the denture plate.

After the to this extent undertaken final positioning of the spatial dimensions of the denture, the latter is final hardened, and if necessary coated as well as lacquered and polished. It is to be understood that if desired individual characteristics are possible by coloring the teeth. For example, red inflamed interdental papillae can be represented, or it is possible to simulate a gray-blue discolored gum border.

The present invention is, of course, in no way restricted to the specific disclosure of the specification and drawings, but also encompasses any modifications within the scope of the appended claims.

What is claimed is:

1. A method of producing dentures, including the steps of:
   introducing a moldable denture plate into the mouth of a patient;
   carrying out a deformation of said denture plate in a patient-specific manner;
   while still in the mouth of said patient , subjecting said denture plate to at least a preliminary hardening;
   removing said denture plate from said patient's mouth; and
   providing said denture plate with prefabricated teeth.

2. A method according to claim 1, wherein said denture plate is incompletely polymerized prior to use, and is deformable at mouth temperature.

3. A method according to claim 1, wherein a biocompatible polymeric material is selected for said denture plate, with said polymeric material being easy to deform in a precise manner, and said polymeric material can be adapted to a mouth situation without a further underlay.

4. A method according to claim 1, wherein a polymeric material that can be light hardened is utilized for said denture plate, said polymeric material being prehardened in the mouth of said patient after deformation.

5. A method according to claim 1, wherein said denture plate is produced as a finished product for use in further manufacture, is then selected for said introducing step, and after deformation in said patient's mouth and hardening of a basal side thereof is filled with an elastic material.

6. A method according to claim 1, wherein said denture plate, after being adapted to a mouth situation, is secured to a bite position holder after a known position determination, or is secured in an articulator via a base that is provided with fastening means and raised portions that are intended for engaging in a deformable material that is applied to a basal side of said denture plate.

7. A method according to claim 1, wherein said denture plate is provided with said teeth in a conventional manner.

8. A method according to claim 1, wherein said teeth are positioned on said denture plate as a combination of teeth that are flexibly interconnected.

9. A method according to claim 1, wherein said teeth are positioned in wax or wax-like polymeric material.

10. A method according to claim 9, wherein said teeth, after checking of a bite position, the tooth position being corrected if required, and wherein to the extent necessary polymeric material is introduced in place of said wax and said polymeric material is polymerized.

11. A method according to claim 1, wherein said teeth are fixed in position relative to the denture plate with material that can be hardened, and wherein the finished denture is hardened and polished.

12. A method according to claim 11, wherein said polymeric material that replaces said wax is prepared in a ready to use state in a tube or injector.

13. A method according to claim 1, wherein a lacquer is applied to the denture plate to achieve a surface having as low of surface roughness as possible and to condition said surface.

14. An articulator comprising:
a retention member including a base (16) provided with a plurality of raised portions (20) for the detachable engagement with a particular elastic material (24) that is carried by a denture plate (26) so that the denture plate and elastic material may be removed from the base without destroying it.

15. An articulator according to claim 14, wherein said retention member includes a support plate that is adjustably mounted.

* * * * *